United States Patent
Juto et al.

(10) Patent No.: US 9,198,618 B2
(45) Date of Patent: Dec. 1, 2015

(54) PRESSURE SENSING SYSTEM AND METHOD

(71) Applicant: CHORDATE MEDICAL AG, Zürich (CH)

(72) Inventors: Jan-Erik Juto, Stockholm (SE); William Holm, Stockholm (SE); Fredrik Juto, Stockholm (SE)

(73) Assignee: CHORDATE MEDICAL AB, Kista (SE)

( * ) Notice: Subject to any disclaimer, the term of this patent is extended or adjusted under 35 U.S.C. 154(b) by 383 days.

(21) Appl. No.: 13/714,636

(22) Filed: Dec. 14, 2012

(65) Prior Publication Data

US 2013/0158426 A1    Jun. 20, 2013

Related U.S. Application Data

(60) Provisional application No. 61/576,804, filed on Dec. 16, 2011.

(30) Foreign Application Priority Data

Dec. 16, 2011 (EP) .................................. 11194062

(51) Int. Cl.
*A61B 5/00* (2006.01)
*A61B 5/03* (2006.01)
(Continued)

(52) U.S. Cl.
CPC ............... *A61B 5/6853* (2013.01); *A61B 5/036* (2013.01); *A61B 5/1076* (2013.01); *A61B 17/12104* (2013.01); *A61B 17/12136* (2013.01); *A61B 17/24* (2013.01)

(58) Field of Classification Search
CPC ............ A61B 17/12136; A61B 17/24; A61B 17/246; A61B 17/12104; A61B 5/1076; A61B 5/036; A61B 5/5852
USPC ..................................... 600/552, 587; 33/512
See application file for complete search history.

(56) References Cited

U.S. PATENT DOCUMENTS 901,376 A    10/1908    Roberts
912,205 A    2/1909    Talcott
(Continued)

FOREIGN PATENT DOCUMENTS

CH    329193 A    4/1958
CN    1524001 A    8/2004
(Continued)

OTHER PUBLICATIONS

Alstadhaug, "Migraine and the Hypothalamus", Cephalalgia, 2009, pp. 1-9.
(Continued)

*Primary Examiner* — Michael C Stout
(74) *Attorney, Agent, or Firm* — Birch, Stewart, Kolasch & Birch, LLP

(57) ABSTRACT

A device for detecting rhinitis in a human subject includes an inflatable member that, in a first state, is configured to be introducible into the nasal cavity of the human subject; an expansion member configured to expand the inflatable member to an expanded, second state within the nasal cavity such that the inflatable member abuts against the tissue of the nasal cavity, and a pressure sensing member configured to measure a pressure exerted on the inflatable member by the tissue of the nasal cavity. A system for detecting rhinitis and methods for analyzing tissue response pressure, detecting rhinitis, predicting the efficacy of a planned rhinitis treatment and evaluating the efficacy of a previous rhinitis treatment are provided.

14 Claims, 4 Drawing Sheets

(51) Int. Cl.
*A61B 17/12* (2006.01)
*A61B 5/107* (2006.01)
*A61B 17/24* (2006.01)

(56) References Cited

U.S. PATENT DOCUMENTS

| | | | |
|---|---|---|---|
| 961,034 | A | 6/1910 | Siebert et al. |
| 1,735,519 | A | 11/1929 | Vance |
| 1,764,838 | A | 6/1930 | Horne |
| 2,052,321 | A | 8/1936 | Smart |
| 2,101,273 | A | 12/1937 | Smith |
| 3,612,211 | A | 10/1971 | Clark, III |
| 3,848,607 | A | 11/1974 | St. Clair |
| 4,462,411 | A | 7/1984 | Rickards |
| 4,911,149 | A | 3/1990 | Borodulin et al. |
| 5,139,510 | A | 8/1992 | Goldsmith, III et al. |
| 5,545,133 | A * | 8/1996 | Burns et al. ............... 604/99.04 |
| 5,609,606 | A | 3/1997 | O'Boyle |
| 5,682,881 | A | 11/1997 | Winthrop et al. |
| 5,903,516 | A | 5/1999 | Greenleaf et al. |
| 6,159,170 | A | 12/2000 | Borodulin et al. |
| 6,193,680 | B1 | 2/2001 | Parsons et al. |
| 6,358,272 | B1 | 3/2002 | Wilden |
| 8,317,816 | B2 | 11/2012 | Becker |
| 2001/0051819 | A1 | 12/2001 | Fischell et al. |
| 2002/0072781 | A1 | 6/2002 | Lattner et al. |
| 2002/0177889 | A1 | 11/2002 | Brisken et al. |
| 2003/0087734 | A1 | 5/2003 | Kring et al. |
| 2004/0097850 | A1 | 5/2004 | Plante |
| 2004/0102722 | A1 | 5/2004 | Naghavi |
| 2004/0112378 | A1 | 6/2004 | Djupesland |
| 2004/0116785 | A1 | 6/2004 | Bulat |
| 2004/0172112 | A1 | 9/2004 | Cioanta et al. |
| 2004/0230252 | A1 | 11/2004 | Kullok et al. |
| 2004/0243172 | A1 | 12/2004 | Hogle |
| 2005/0005942 | A1 | 1/2005 | Aylsworth et al. |
| 2005/0011518 | A1 | 1/2005 | Biondo et al. |
| 2005/0021092 | A1 | 1/2005 | Yun et al. |
| 2005/0054958 | A1 | 3/2005 | Hoffmann |
| 2006/0063973 | A1 * | 3/2006 | Makower et al. ............. 600/114 |
| 2006/0094992 | A1 | 5/2006 | Imboden et al. |
| 2006/0095065 | A1 * | 5/2006 | Tanimura et al. ............. 606/194 |
| 2006/0190022 | A1 * | 8/2006 | Beyar et al. ................. 606/192 |
| 2007/0149905 | A1 | 6/2007 | Hanna |
| 2008/0015540 | A1 * | 1/2008 | Muni et al. .................. 604/500 |
| 2008/0172033 | A1 * | 7/2008 | Keith et al. .................. 604/506 |
| 2008/0198330 | A1 | 8/2008 | Taylor |
| 2008/0200848 | A1 | 8/2008 | Avni |
| 2008/0208168 | A1 | 8/2008 | Garabet |
| 2008/0281238 | A1 | 11/2008 | Oohashi et al. |
| 2009/0005713 | A1 | 1/2009 | Podrazhansky et al. |
| 2009/0076439 | A1 * | 3/2009 | Dollar et al. ................... 604/28 |
| 2009/0187098 | A1 | 7/2009 | Makower et al. |
| 2009/0312740 | A1 * | 12/2009 | Kim et al. .................... 604/500 |
| 2010/0004709 | A1 | 1/2010 | Mische |
| 2010/0094209 | A1 * | 4/2010 | Drasler et al. ............. 604/95.04 |
| 2010/0121270 | A1 * | 5/2010 | Gunday et al. ............. 604/98.01 |
| 2010/0191215 | A1 * | 7/2010 | Globerman et al. .......... 604/500 |
| 2010/0228075 | A1 | 9/2010 | Lu |
| 2010/0234840 | A1 | 9/2010 | Jackson et al. |
| 2010/0249637 | A1 | 9/2010 | Walter et al. |
| 2010/0274188 | A1 * | 10/2010 | Chang et al. ............... 604/96.01 |
| 2010/0286576 | A1 | 11/2010 | Pryor et al. |
| 2011/0190668 | A1 | 8/2011 | Mishelevich |
| 2011/0270138 | A1 | 11/2011 | Mishelevich |
| 2012/0259217 | A1 * | 10/2012 | Gerrans et al. ............... 600/435 |

FOREIGN PATENT DOCUMENTS

| | | |
|---|---|---|
| CN | 1964755 A | 5/2007 |
| CN | 101208127 A | 6/2008 |
| EP | 0935980 A1 | 8/1999 |
| FR | 592104 A | 7/1925 |
| FR | 838034 A | 2/1939 |
| FR | 920885 A | 4/1947 |
| GB | 385992 A | 1/1933 |
| GB | 1217760 A | 12/1970 |
| JP | 2001-17500 A | 1/2001 |
| JP | 2001-37883 A | 2/2001 |
| KR | 10-1019957 B1 | 3/2011 |
| RU | 2099039 C1 | 12/1997 |
| RU | 2199303 C1 | 2/2003 |
| SU | 1148614 A | 4/1985 |
| SU | 1560205 A1 | 4/1990 |
| WO | WO 86/01399 A1 | 3/1986 |
| WO | WO 96/36396 A2 | 11/1996 |
| WO | WO 96/39218 A1 | 12/1996 |
| WO | 01/35846 A1 | 5/2001 |
| WO | WO 01/41695 A2 | 6/2001 |
| WO | WO 2004/047675 A2 | 6/2004 |
| WO | WO 2004/105579 A2 | 12/2004 |
| WO | WO 2006/114783 A2 | 11/2006 |
| WO | WO 2008/138997 A1 | 11/2008 |
| WO | WO 2010/033055 A1 | 3/2010 |
| WO | 2011/014530 A2 | 2/2011 |

OTHER PUBLICATIONS

Ansarinia et al., "Electrical Stimulation of Sphenopalatine Ganglion for Acute Treatment of Cluster Headaches", Headache, Jul. 2010, pp. 1164-1174.

Bar-Shir et al., "Late Stimulation of the Sphenopalatine-Ganglion in Ischemic Rats: Improvement in N-Acetyl-Aspartate Levels and Diffusion Weighted Imaging Characteristics as Seen by MR", Journal of Magnetic Resonance Imaging, vol. 31, 2010, pp. 1355-1363.

Brown et al., "Towards a Physiology-Based Measure of Pain: Patterns of Human Brain Activity Distinguish Painful from Non-Painful Thermal Stimulation", Plos One, vol. 6, Iss. 9, e24124, Sep. 2011, pp. 1-8.

Kim et al., "Predicting the Timing of Spikes Evoked by Tactile Stimulation of the Hand", J Neurophysiol, vol. 104, 2010, pp. 1484-1496.

Krajnak et al., "Characterization of Frequency-Dependent Responses of the Vascular System to Repetitive Vibration", JOEM, vol. 52, No. 6, Jun. 2010, pp. 584-594.

Kuncel et al., "Selection of Stimulus Parameters for Deep Brain Stimulation", Clinical Neurophysiology, vol. 115, 2004, pp. 2431-2441.

Leroux et al., "Cluster Headache", Orphanet Journal of Rare Diseases, vol. 3, No. 20, 2008, 11 pages provided.

Ludwig, "The Velocity of Sound through Tissues and the Acoustic Impedance of Tissues", The Journal of the Acoustical Society of America, vol. 22, No. 6, Nov. 1950, 5 pages provided.

Malm, "Measurement of Nasal Patency", Allergy, vol. 52 (suppl. 40), 1997, pp. 19-23.

Malm, "Stimulation of Sympathetic Nerve Fibres to the Nose in Cats", Acta Otolaryng, vol. 75, 1973, pp. 519-526.

Salansky et al., "Responses of the Nervous System to Low Frequency Stimulation and EEG Rhythms: Clinical Implications", Neuroscience and Biobehavioral Reviews, vol. 22, No. 3, 1998, pp. 395-409.

Tepper et al., "Acute Treatment of Intractable Migraine With Sphenopalatine Ganglion Electrical Stimulation", Headache, vol. 49, Jul. 2009, pp. 983-989.

VBM, "VBM Tube Fixations", VBM Medizintechnik GmbH, 2006, 6 pages provided.

Zelena, "Nerves and Mechanoreceptors: The Role of Innervations in the Development and Maintenance of Mammalian Mechanoreceptors", Springer, 1994, pp. 147-148.

Klinger et al., "Untersuchungen zur Mikro-zirkulation der Nasenschleimhaut bei Verwendung von Ballon-tamponaden", Laryngo-Rhino-Otol., vol. 76, 1997, pp. 127-130, XP008066107.

Papon et al., "Nasal wall compliance in vasomotor rhinitis," J. Appl. Physiol., vol. 100, 2006 (First published Sep. 1, 2005), pp. 107-111, XP055055268.

* cited by examiner

PRESSURE SENSING SYSTEM AND METHOD

CROSS-REFERENCE TO RELATED APPLICATIONS

This application claims priority under 35 U.S.C. §119(e) to U.S. Provisional Application No. 61/576,804, filed on Dec. 16, 2011. This application also claims priority under 35 U.S.C. §119(a) to Application No. 11194062.3, filed in Europe on Dec. 16, 2011. The entirety of each of the above-identified applications is expressly incorporated herein by reference.

BACKGROUND OF THE INVENTION

1. Field of the Invention

The present invention relates to devices, systems and methods for detecting rhinitis. The present invention moreover relates to methods for predicting the efficacy of a rhinitis treatment to be performed, as well as to methods for evaluating the efficacy of a previously performed rhinitis treatment 2. Description of Background Art Rhinitis, commonly referred to as a stuffy nose, can generally be categorized into two groups: allergic rhinitis and non-allergic rhinitis. Differentiating allergic rhinitis from other causes of rhinitis can be difficult because the diagnostic criteria for various forms of rhinitis are not always clear-cut. Accurate diagnosis is however important because therapies that are effective for allergic rhinitis (i.e. antihistamines and nasal corticosteroids) may be less effective for other types of rhinitis. Allergic rhinitis includes episodic rhinitis; occupational rhinitis (allergen); perennial rhinitis and seasonal rhinitis. Non-allergic rhinitis includes atrophic rhinitis; chemical- or irritant-induced rhinitis; drug-induced rhinitis such as induced by antihypertensive medications, aspirin, non-steroidal anti-inflammatory drugs and oral contraceptives, and rhinitis medicamentosa; emotional rhinitis; exercise-induced rhinitis; gustatory rhinitis; hormone-induced rhinitis such as induced by hypothyroidism, menstrual cycle, oral contraceptives and pregnancy; infectious rhinitis such as acute (usually viral) rhinitis, chronic (rhino sinusitis); non-allergic rhinitis with eosinophilia syndrome; occupational rhinitis (irritant); perennial non-allergic rhinitis such as vasomotor rhinitis; postural reflexes primary ciliary dyskinesia, and reflux-induced rhinitis or gastroesophageal reflux disease. If the patient has severe symptoms or an unclear diagnosis, or if he or she is a potential candidate for allergen avoidance treatment or immunotherapy, an allergy test should be performed. A comprehensive history and physical examination should however be used to help diagnose the cause of rhinitis.

Different methods are known for generally studying nasal patency, i.e. nasal openness and/or airflow, without necessarily resulting in diagnosis. Malm lists a number of these methods (Maim, L., Allergy, 1997; 52:19-23), which include computed tomography, magnetic resonance imaging, volumetry, rhino stereometry, acoustic rhinometry, rhinomanometry and nasal peak flow.

Devices and methods are known for generally measuring an inner diameter of a body lumen, such as the devices and methods disclosed in U.S. Application Publication No. 2010/0234840. The method includes inserting a balloon in a body lumen, such as the esophagus, inflating the balloon inside the body lumen using an expansion medium; and monitoring a mass of the expansion medium inside the balloon. Wall compliance of an esophagus can moreover be determined by measuring the total fluid within the balloon at two different static pressures and calculating the wall compliance based on the variation in fluid between the first and the second static pressure.

In WO 2004/047675 there are disclosed devices and methods for measuring changes in tissue elasticity. The disclosed device includes a catheter with an expandable element at a proximal end. The catheter is moved longitudinally and circumferentially within a cavity such as an artery and changes in elasticity are detected by measuring changes in pressure. The catheter may be further equipped with sensors for measuring temperature and pH. This method is described to be useful for characterizing vulnerable plaque and cancer tissue.

SUMMARY OF THE INVENTION

It is an object of the present invention to provide novel devices and systems for detecting rhinitis. It is moreover an object of the present invention to provide novel devices, systems and methods for detecting rhinitis, predicting the efficacy of a planned rhinitis treatment and evaluating the efficacy of a previous rhinitis treatment.

In a first aspect of the invention, there is provided a device for detecting rhinitis in a human subject, comprising: an inflatable member that, in a first state, is configured to be introducible into the nasal cavity of the human subject; an expansion member configured to expand the inflatable member to an expanded, second state within the nasal cavity such that the inflatable member abuts against the tissue of the nasal cavity; and a pressure sensing member configured to measure a pressure exerted on the inflatable member by the tissue of the nasal cavity. The expansion member may comprise a tubular structure comprising an end portion arranged freely within said inflatable member and comprising at least one opening for fluid communication with the inflatable member.

By introducing and expanding the inflatable member into the nasal cavity of a human subject, a pressure is applied onto the tissue. Both healthy subjects and subjects suffering from a form of rhinitis respond to the applied pressure. The response to the applied pressure is monitored by the pressure sensing member as changes in the pressure exerted on the inflatable member by the tissue over a period of time. In both healthy subjects and subjects suffering from rhinitis, a steep decrease in the measured pressure is initially observed. Thereafter, sudden pressure decreases are observed in all subjects until a saturation pressure is reached. In between the pressure decreases, there are periods of nearly constant pressure. These pressure decreases are believed to correspond to sphincters opening up and, as a consequence, a corresponding decrease in blood filling of the nasal mucosa. When the abovementioned saturation pressure is reached, the applied pressure may be reduced. This leads to a smooth recovery in the measured pressure to a second saturation pressure. This is believed to correspond to refilling of the vessels and resumed function of the sphincters.

It has been found by the inventors that the tissue response pressure in the nasal cavity over time is different in a subject suffering from rhinitis than in a healthy subject. By measuring the tissue response pressure over time with a device according to the first aspect of the present invention, rhinitis may consequently be detected. In addition, the device may be used for evaluating the efficacy of a previously performed rhinitis treatment, i.e. for evaluating whether or not a patient has been cured from his/her rhinitis or whether the symptoms have been alleviated. The device may moreover be used for predicting efficacy of a planned rhinitis treatment, i.e. for predicting e.g. the probability of a certain patient responding to the treatment.

For detecting, evaluating and predicting as described above, it may be useful to create a measured tissue response pressure curve reflecting the changes in measured tissue response pressure over time, and to compare that measured pressure curve to a reference pressure curve, reflecting for example the changes in tissue response pressure over time in the nasal cavity of a healthy human subject.

The tissue response to an applied static pressure, e.g. as exerted on the inflatable member as described above, is herein generally referred to as a measured pressure or a tissue response pressure. Correspondingly, a curve reflecting the changes in measured tissue response pressure over time is herein generally referred to as a measured pressure curve. The pressure exerted by tissue onto the inflatable member can be measured as the pressure within the inflatable member in embodiments wherein the circumference of the inflatable member defines an inner chamber. Such a pressure is referred to as the inner pressure of the inflatable member.

In another embodiment of the first aspect, there is provided a device wherein said inflatable member in the second state is configured to abut against the tissue of the nasal cavity at a pressure of between approximately 100 and 180 mbar. This pressure represents the initially applied pressure on the tissue. As discussed above, the application of a specific pressure onto the tissue in the nasal cavity influences the nasal tissue in a specific way which is reflected in tissue response pressure as measured by the pressure sensing member. The initially applied pressure may lie in the range of from 120 to 160 mbar, such as from 130 to 150 mbar. In some cases, the applied pressure may be 140 mbar.

The pressure sensing member may for instance be positioned within the inflatable member, such that the inflatable member comprises at least a portion of the pressure sensing member. Such a pressure sensing member may for example be located on the surface of the inflatable member.

The device may further comprise a display member configured to display the pressure measured by the pressure sensing member, i.e. the tissue response pressure. A display member, such as an LCD panel, facilitates monitoring of the tissue response pressure by an operator. Such display may either show a current value of the tissue response pressure only, or may alternatively or also show how the tissue response pressure develops over time. In other words, the display member is in one embodiment configured to display the pressure measured by the pressure sensing member as a function of time. The display member may be digital or analog. In case the display member only shows a current value of the tissue response pressure, the operator has to monitor the time development of the signal in order to be able to draw any conclusions regarding the nasal pathology. If the development of the tissue response pressure over time is shown, e.g. on a computer screen or on an XY-plotter, the evaluation of nasal pathology for the operator is facilitated. In both cases however, it is the operator who, based on experience and/or training, draws conclusions regarding the health of the patient.

In another embodiment of the first aspect, the expansion member comprises a pressure generator for increasing the pressure within the inflatable member, and a closing valve. The closing valve is used to form a closed system of the inflatable member and at least a part of the expansion member when the desired pressure has been applied. Furthermore, the pressure sensing member may be arranged externally of and/or separately from the stimulation member, for example such that it is integrated with the expansion member, while being configured to measure the internal air pressure in the closed system.

In another embodiment of the first aspect, the inflatable member is connectable to a vibration generating member which is configured to bring the inflatable member to vibrate such that vibrations are imparted to the tissue of the nasal cavity. Vibrations may be imparted to the nasal tissue for different purposes. Not only may vibrations be applied for treatment of the nasal mucosa, but also for studying tissue compliance. Monitoring changes in measured tissue pressure during vibration stimulation in the nasal cavity may give an indication of the progress of vibration treatment, and possibly recovery of the nasal tissue, as well as an estimate of tissue compliance.

In another aspect of the present invention, there is provided a system for detecting rhinitis, comprising: a data collection module configured to obtain an input signal reflecting a tissue response pressure of the nasal cavity of a human subject; a pressure analyzing module configured to analyze said input signal to identify plateaus and decreases in the signal over a period of time; and a rhinitis detection module configured to detect rhinitis by comparing said plateaus and decreases in the signal over time with at least one predetermined boundary condition.

The rhinitis detecting system of the second aspect may be used for detecting rhinitis in a human subject, and, in similarity to the above defined device, be useful for predicting the efficacy of a planned rhinitis treatment as well as for evaluating the efficacy of a previously conducted rhinitis treatment.

The data collection module is arranged to obtain an input signal reflecting a tissue response pressure and to collect the individual values of the input signal over time. The pressure analyzing module analyzes the signal in order to identify changes. Such changes are pressure plateaus and decreases, whereas the pressure plateaus correspond to periods of nearly constant pressure in between the pressure decreases as discussed in connection with the device aspect. The collected tissue response pressure of a human subject exhibits pressure plateaus and decreases that are characteristic for the health condition of the human subject in question. Thus, the pressure plateaus and decreases corresponding to a certain patient suffering from rhinitis are different from those of a healthy subject. This enables detection of rhinitis by comparing the plateaus and decreases of a certain human subject with a boundary condition.

A boundary condition may for example correspond to a calculated value or an average value obtained from a number of measurements of tissue response pressure. Non-limiting examples of boundary conditions useful for the detection of rhinitis are, among others, a tissue response pressure corresponding to a final saturation plateau, a slope of a specific decrease in tissue response pressure, a length of a specific tissue response plateau, a tissue response pressure obtained after a predetermined period of time, the time period for reaching a predetermined pressure plateau, the number of pressure decreases before reaching a saturation pressure and the number of plateaus before reaching a saturation pressure. In one example, the system according to the present invention may further comprise a boundary determining module configured to determine from at least one reference pressure curve at least one boundary condition.

In another embodiment, the pressure analyzing module is configured to characterize said plateaus and decreases of the signal by at least one curve property selected from amplitude, rate of change and frequency. The amplitude here refers to the length of the pressure decreases, expressed in pressure units or in time. The rate of change is the slope of the decreases, whereas the frequency refers to the number of decreases per time unit. By definition of such specific curve properties, the detection of rhinitis can be made easier. The tissue response pressure curve of a healthy subject typically demonstrates a distinctive number of decreases and plateaus before reaching a final saturation pressure, whereas the tissue response pressure curves of subjects suffering from different forms of rhinitis typically demonstrate either a higher number of decreases and plateaus or a lower number of decreases and plateaus. Correspondingly, the curve properties of a tissue response pressure curve of a healthy subject may be distinguished from the curve properties of tissue response pressure curves of subjects suffering from rhinitis. The curve properties of the measured tissue response pressure curve may consequently be compared to specific boundary conditions for detection of rhinitis. Non-limiting examples of boundary conditions specific for the curve properties amplitude, rate of change and frequency are a maximum threshold ($threshold_{max}$) for a specific curve property and a minimum threshold ($threshold_{min}$) for a specific curve property. Thus, in another embodiment, the rhinitis detection module is configured to detect a first and second subtype of rhinitis by finding portions of at least one of the curve properties having individual values above a predetermined $threshold_{max}$ for that particular curve property to detect a first subtype of rhinitis, and by finding portions of at least one of the curve properties having individual values below a predetermined $threshold_{min}$ for that particular curve property to detect a second subtype of rhinitis.

The pressure analyzing module thus has the capability to detect the above mentioned features of the input signal. In addition, the pressure analyzing module may have further processing capability which may allow the module to recognize and compare curve patterns.

In yet another embodiment, the pressure analyzing module is further configured to detect peaks corresponding to sneezes in the input signal. Imparting vibrations to the nasal cavity may provoke sneezing. Such sneezes are registered as peaks in the measured tissue response pressure. The frequency of sneezes can give further indication of the health condition of the human subject in question.

The input signal reflecting a tissue response pressure of the nasal cavity of a human subject corresponds, in another embodiment, to the pressure exerted by tissue of the nasal cavity on a device according to the definition in connection with the first aspect of the present invention. More specifically, the tissue response pressure may correspond to the pressure exerted on a device connectable to a vibration generating member. Thus, the input signal reflects a tissue pressure influenced by vibrations as exerted on a vibrating inflatable member. Such an example system may further comprise a compliance determining module configured to determine the compliance of the tissue to imparted vibrations. As used herein, the term compliance refers to a measure of the tendency of the nasal cavity to resist recoiling toward its original dimensions upon removal of, e.g. an inflatable member and is the reciprocal of "elastance."

In yet another embodiment of the system aspect, the system comprises a device as defined in relation to the device aspect of the present invention.

In embodiments wherein the input signal reflecting a tissue response pressure corresponds to the pressure exerted on a vibrating inflatable member, the number of peaks in the pressure curve may be observed. Those peaks correspond, as previously discussed, to the human subject sneezing and may typically be observed in human subjects suffering from rhinitis. The number of peaks may thus be utilized for further specifying the subject's health condition. The pressure analyzing module of the system may for instance be configured to determine whether the peak frequency surpasses a predetermined peak threshold. When comprising a device according to the device aspect of the present invention, the system may in addition comprise a control member configured to terminate the vibration stimulation and pressure measurement when said peak threshold is surpassed.

The system may moreover comprise a storing module configured to store, e.g. boundary conditions, thresholds and reference curves. To facilitate patient follow up, such a storing module may moreover enable storing of tissue response pressure curves and derived curve properties for a particular human subject.

It should be understood that embodiments and examples described in relation to a particular aspect of the present invention are equally relevant, when applicable, to the other aspects of the present invention.

In another aspect of the present invention, there is provided a method for analyzing tissue response pressure, comprising: providing a tissue response pressure curve reflecting the tissue response pressure of a nasal cavity of a human subject over a period of time; providing a reference pressure curve reflecting a reference tissue response pressure of the nasal cavity over a reference period of time; and comparing said tissue response pressure curve with said reference pressure curve to assess correspondence between said tissue response pressure curve and reference pressure curve. This aspect of the invention is referred to as the first method aspect of the invention.

By assessing the correspondence between a tissue response pressure curve and a reference curve, one might identify deviation from a certain condition of a human subject as represented by the reference curve. The analyzing method can function as a preparatory method for identifying deviation prior to actually determining the condition of a human subject. Thus, depending on the desired assessment for a particular patient, a suitable reference curve may be provided. By comparing the development of tissue response pressure over time with a reference curve, a lot of information on a subject's health condition can potentially be derived, as compared to a case where only one or two tissue response pressure values are extracted. Rhinitis is a complex condition and a lot of information may be required to enable a correct diagnosis.

In one embodiment, the method further comprises one of: detecting rhinitis by comparing a tissue response pressure curve obtained from a human subject possibly suffering from rhinitis to said reference pressure curve; predicting efficacy of a rhinitis treatment by comparing a tissue response pressure curve obtained from a human subject prior to rhinitis treatment to said reference pressure curve, or evaluating the efficacy of a previously performed rhinitis treatment by comparing a tissue response pressure curve obtained from a human subject previously subjected to rhinitis treatment to said reference pressure curve. It should be understood that the reference pressure curve may be different depending on the purpose of the determination. If the comparison is made to detect rhinitis, then the reference pressure curve may represent a healthy condition. If the comparison is made to predict the outcome of any planned treatment regime, the reference pressure curve may be representative of a health condition known to respond well to the planned treatment in question. If the comparison on the other hand is made to evaluate the efficacy of any previously performed rhinitis treatment, the reference pressure curve may also represent a healthy condition or correspond to a pressure response curve obtained prior to said treatment. It should be noted that the method may be useful for evaluating or predicting the efficacy of any previous or planned rhinitis treatment.

Should the finding of the abovementioned method be that the human subject suffers from rhinitis or that a previous rhinitis treatment has not efficiently treated the rhinitis, a rhinitis treatment may be recommended. Such rhinitis treatment is hence performed separately from the method of the present invention, and may for example be performed in accordance with the method as described in WO 2008/138997, which is incorporated herein by reference and which includes vibration stimulation of the nasal passage, among other body cavities, in order to treat, for example rhinitis.

The method according to the present invention thus provides objective quantitative measures of the various conditions collectively referred to as rhinitis. This is lacking in the clinical practice today. Being able to find the right diagnosis may even restrain or stop patients from (over) using inefficient medications. Furthermore, it is possible to follow the development of the condition over time and thus to determine whether a specific treatment is effective or not.

In another embodiment of the first method aspect, said reference pressure curve is selected from a previously obtained tissue response pressure curve; an average of at least two previously obtained tissue response pressure curves; a fit of a model to at least one measured tissue response pressure curve, and a theoretically calculated reference pressure curve. The reference pressure curve is thus selected from a predetermined reference pressure curve, but may in some instances be created, while performing the method, from any of the above listed curves or models. It should further be understood that the previously obtained tissue response pressure curves may derive from the same human subject or from another human subject, depending on the circumstances. Further, the theoretically calculated reference pressure curve is calculated without directly relying upon a measured tissue response pressure, thus, it might e.g. be calculated from any known pressure curve. A model that can be fit to measured data is a parameterized representation of the expected general shape of a tissue response pressure curve. Use of such a model may eliminate noise from the curve and consequently make the characteristics of the curve more clear.

The comparative step of the method comprises, in another embodiment, at least one of the following: determining that the tissue response pressure curve corresponds to said reference pressure curve or lies within a predetermined tolerance interval; determining that at least parts of the tissue response pressure curve exceed said tolerance interval, and determining that at least parts of the tissue response pressure curve fall below said tolerance interval. Should the tissue response pressure curve fall outside of the defined tolerance interval of a healthy condition, it can, e.g. be concluded that the human subject suffers from rhinitis or has not been efficiently treated for his or her rhinitis. A tissue response pressure curve that at least partly surpasses the tolerance interval may indicate a subtype of rhinitis, whereas a tissue response pressure curve that at least partly falls below the tolerance interval may indicate another subtype of rhinitis. In this case, the tolerance interval may reflect a normal distribution around a particular health condition.

In another embodiment of the method, said providing a tissue response pressure curve is selected from obtaining time and tissue response pressure value pairs, and fitting a model to individual values. By fitting a model to the individual values, the comparison to a reference curve may be easier to perform, especially if the reference curve is formulated in the same way. This can furthermore be an efficient way to remove noise from the signal.

In a further embodiment, the tissue response pressure curve is created by collecting an input signal reflecting a tissue response pressure of the nasal cavity of a human subject over a period of time.

In a related aspect of the present invention, there is provided a method for detecting rhinitis, comprising: introducing an inflatable member into a nasal cavity of a human subject; expanding the inflatable member within the nasal cavity such that the inflatable member abuts against a tissue of the nasal cavity; measuring a pressure exerted on the inflatable member by the tissue of the nasal cavity over a period of time to create a measured pressure curve; and analyzing the measured pressure curve to detect rhinitis. This aspect of the invention is referred to as the second method aspect. By using this method, a physician can measure the nasal pathology and in an objective way differentiate between different forms of rhinitis. It may also be possible to follow the development over time for a particular patient to detect long term changes in the patient's state of health.

In another related aspect of the present invention, there is provided a method for evaluating the efficacy of a previously performed rhinitis treatment, comprising: introducing an inflatable member into a nasal cavity of a human subject; expanding the inflatable member within the nasal cavity such that the inflatable member abuts against a tissue of the nasal cavity; measuring a pressure exerted on the inflatable member by the tissue of the nasal cavity over a period of time to create a measured pressure curve; and analyzing the measured pressure curve to evaluate the efficacy of the previous rhinitis treatment. This aspect of the invention is referred to as the third method aspect. By using this method, one can determine if an administered treatment is having the desired effect, and if not the treatment can altered, replaced, or aborted. In this way, the risk of overusing pharmaceuticals can be reduced.

In yet another related method aspect of the present invention, there is provided a method for predicting the efficacy of a rhinitis treatment, comprising: introducing an inflatable member into a nasal cavity of a human subject; expanding the inflatable member within the nasal cavity such that the inflatable member abuts against a tissue of the nasal cavity; measuring a pressure exerted on the inflatable member by the tissue of the nasal cavity over a period of time to create a measured pressure curve; and analyzing the measured pressure curve to predict the efficacy of rhinitis treatment. This aspect of the invention is referred to as the fourth method aspect of the invention. This method may be useful for predicting the outcome of a specific rhinitis treatment and consequently for selecting the most suitable treatment for a particular human subject.

In the following, a number of embodiments of the four method aspects will be described.

In one embodiment, preferably relevant to the second, third and fourth method aspects, said analyzing comprises identifying plateaus and decreases in said measured pressure curve, and comparing said plateaus and decreases to at least one predetermined boundary condition. Thus, as previously discussed in connection with the system aspect, the collected tissue response pressure from a human subject exhibits pressure plateaus and decreases that are characteristic for the health condition of the subject in question. In this manner, detection of rhinitis is enabled by comparing the plateaus and decreases of a certain human subject with the boundary condition. The boundary condition may correspond to a calculated value or an average value obtained from a number of measurements of tissue response pressure as previously discussed. A number of non-limiting examples of boundary conditions relevant for detection of rhinitis are listed above.

These examples of boundary conditions are however equally relevant for predicting the efficacy of a planned rhinitis treatment and for evaluating the efficacy of a previously conducted rhinitis treatment. The methods may moreover comprise determining from at least one reference pressure curve at least one boundary condition.

In other embodiments of the method aspects, the methods may comprise characterizing said plateaus and decreases by at least one curve property selected from amplitude, rate of change and frequency. This may enable an alternative, possibly more precise, determination of the health condition of the human subject, in accordance with the pressure analysis of the system aspect as described above. Consequently, in another embodiment, a subtype of rhinitis is detected by determining whether any individual values of any one of the curve properties surpasses a predetermined threshold$_{max}$ for that particular curve property. Similarly, in another embodiment, a subtype of rhinitis is detected by determining whether any individual values of any one of the curve properties goes below a predetermined threshold$_{min}$ for that particular curve property.

As part of the analyzing described above, a reference pressure curve may be provided and the measured pressure curve may be compared to the reference pressure curve. The reference pressure curve may be selected from a previously obtained measured pressure curve; an average of at least two previously obtained measured pressure curves; a fit of a model to at least one measured pressure curve, or a theoretically calculated reference pressure curve, in accordance with the description in connection to the first method aspect. The comparison between the measured pressure curve and the reference pressure curve may be done in order to either determine whether the measured pressure curve corresponds to the reference pressure curve or lies within a predetermined tolerance interval; determine whether at least parts of the measured pressure curve exceed the tolerance interval, or determine whether at least parts of the measured pressure curve fall below the tolerance interval.

In another embodiment, said creating of a measured pressure curve comprises either storing time and pressure value pairs or fitting a model to time and pressure value pairs.

The measured pressure curve may thus be obtained from pressure measurements conducted in the nasal cavity of a human subject. In addition to the pressure measurements conducted in the nasal cavity, the methods may further comprise imparting vibrations to the tissue in the nasal cavity via the inflatable member. By conducting vibration stimulation in the nasal cavity at the same time as the pressure exerted by tissue on the inflatable member is measured, the measured pressure will not only provide information on a subject's health condition, but also information on tissue compliance to imparted vibrations. Therefore, in another embodiment of the method aspects, the methods comprise determining compliance of the tissue to the imparted vibrations.

In yet another embodiment, the methods comprise detecting peaks corresponding to sneezes in the tissue response pressure curve or in the pressure exerted on the inflatable member. As previously discussed, should the peak frequency surpass a predetermined peak threshold, this may be an indication of a particular health condition of the human subject.

When expanded within the nasal cavity, an inflatable member may abut against the tissue of the nasal cavity at a pressure of between approximately 100 and 180 mbar, for instance from 120 to 160 mbar, such as from 130 to 150 mbar. This corresponds to the pressure applied when initiating the pressure measurements in the nasal cavity.

Pressure measurements may conveniently be conducted in the nasal cavity during a time period of between approximately 1 and 10 minutes.

In particular embodiments of the method aspect, the inflatable member may be comprised within a device or a system as defined in the device and system aspects of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
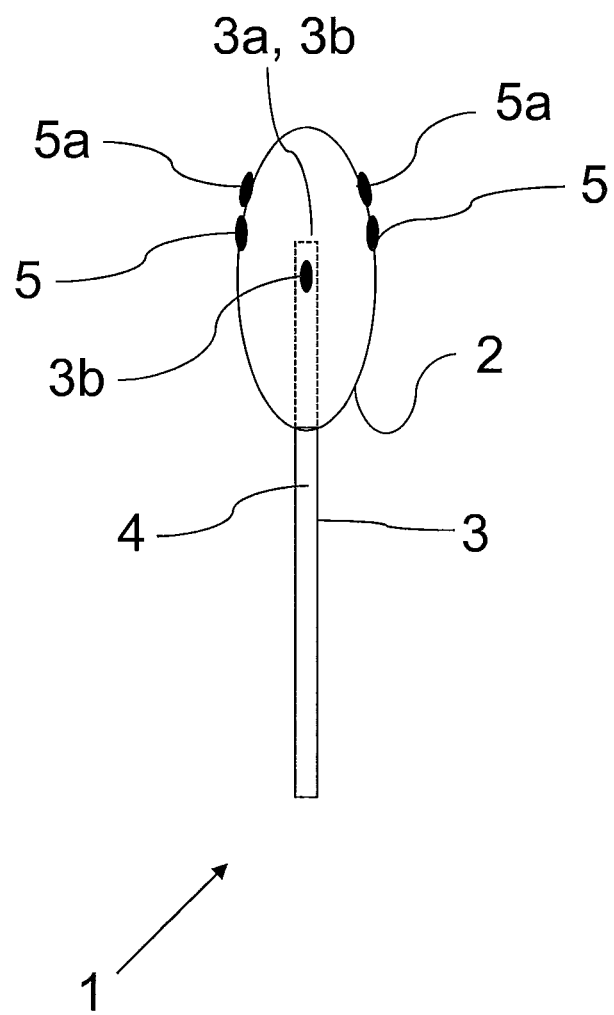
FIG. 1 is a schematic representation depicting an example of a device according to the device aspect of the present invention.

The present invention will now be described with reference to the accompanying drawings, wherein the same or similar elements are identified with the same reference numeral.

With reference to FIG. 1, a specific example of a device according to the device aspect of the present invention will now be discussed. The device 1 for detection of rhinitis in a human subject has two configurations, or states, wherein FIG. 1 depicts a second configuration, or state, of the device. The inflatable member 2 is, in its expanded state, arranged to partly surround an expansion member 3, such that the end portion of the expansion member 3 is located inside the inflatable member 2. The inflatable member 2 is for example a balloon made of a material such as plastic or rubber. In some instances, the inflatable member is made of latex.

The expansion member 3 comprises at least one channel 4 for supply of fluid to the inflatable member 2. The inflatable member 2 thus comprises a chamber for containing fluid, e.g. gas or liquid, supplied by the expansion member 3. The chamber walls are defined by the inner surface of the inflatable member 2. The supply of fluid to the inflatable member 2 via the expansion member 3 thus influences the volume and degree of expansion of the inflatable member 2. To allow free passage of fluid from the expansion member 3 to the inflatable member 2, the end portion 3a of the expansion member 3 comprises at least one opening 3b. If the end portion 3a of the expansion member 3 is arranged freely within the inflatable member 2, as for example depicted in FIG. 1, the end portion 3a may comprise more than one opening 3b for supply of fluid to the inflatable member 2. The opening(s) 3b can be arranged around a perimeter of the end portion 3a of the expansion member 3 and/or can be arranged in an axial direction at the terminus of end portion 3a of the expansion member 3. The opening(s) 3b can be distributed along a longitudinal direction of the portion of the expansion member 3 that is located within the inflatable member 2. Examples of an expansion member comprising at least one channel 4 include a pipe, a tubing, a conduit, a cylinder, a tube, etc. The expansion member 3 may for instance be made of a plastic, rubber or metal material.

Alternative arrangements of an inflatable member 2 and an expansion member 3 are anticipated, wherein the inflatable member 2, for example is connected adjacent to the end portion 3a of the expansion member 3 or arranged as a sleeve around the expansion member 3 some distance away from the end portion 3a. The parts of the expansion member 3 and inflatable member 2 in contact with the human body typically define a closed system to prevent leakage of fluid to the human body.

Two pressure sensors 5 are optionally arranged on the outer surface of the inflatable member 2. This arrangement of pressure sensors 5 enables accurate measuring of a tissue response pressure as exerted on the surface of the inflatable member 2 when the inflatable member 2 is arranged in its second expanded state within the nasal cavity of a human subject. In this example of a device 1, two pressure sensors 5 are present, however, it should be understood that the device 1 may comprise any suitable number of pressure sensors 5, such as a plurality of pressure sensors 5 arranged around the circumference of the inflatable member. One example of a pressure sensor 5 that may be arranged on the surface of the inflatable member is a strain gauge. Such a strain gauge may be applied onto the surface, e.g. with glue or by evaporation.

Alternatively, a pressure sensor 5 may be integrated within the inflatable member 2. The pressure inside the inflatable member 2 is proportional to the pressure exerted by the tissue onto the outer surface of the inflatable member 2 and a pressure sensor 5 may thus measure the inner pressure of the inflatable member 2. One example of an integrated pressure sensing member is a MEMS (Micro-Electro-Mechanical System) device.

Expansion of the inflatable member 2 may, for example be achieved by increasing the air pressure within the inflatable member 2. The expansion member 3 may comprise a pressure generator, e.g. a syringe, a balloon, or a pump, arranged to increase the air pressure within the inflatable member. In such cases, the tissue response pressure may be measured by monitoring the air pressure within the inflatable member 2. A pressure sensor 5 may for example be arranged externally of the inflatable member 2 and in fluid communication with the channel 4. A manually operated pumping bulb equipped with a manometer and a closing valve may be used as a pressure generator. An exemplary mode of operation is to inflate the inflatable member 2 to a pressure in the range of 100 to 180 mbar by manually squeezing the pumping bulb, closing the valve, and observing the time evolution of the air pressure within the inflatable member 2 as shown on the manometer.

In some examples, vibrations may be applied by changing the air volume within the device 1. The tissue response pressure as registered by the pressure sensors 5 can thus give an estimate of the compliance of the tissue surrounding the inflatable member 2. This may give an indication on how the human subject in question would respond to a rhinitis treatment, e.g. a vibrational rhinitis treatment as disclosed in WO 2008/138997.

In other examples of a rhinitis detection device, other types of sensing elements can be integrated in the device. The inflatable member 2 can, for example be provided with separate sensors 5a for either one of temperature, pH, and/or electrical conductivity. Such sensors can be attached to the outside surface of the inflatable member 2 or be integral with the inflatable member 2 as described above with regard to the pressure sensors 5. By receiving such data in addition to the measured pressure, further characterization of nasal pathology may be possible.

Figure 2:
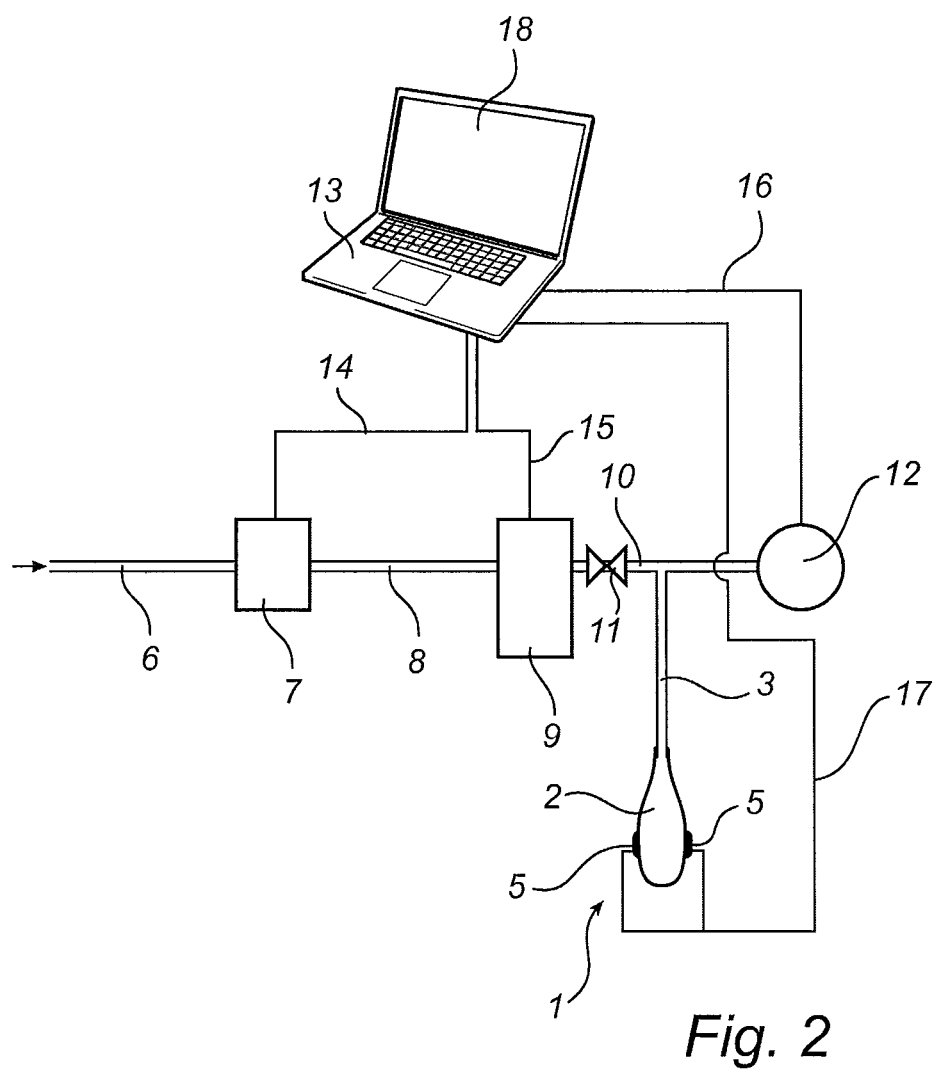
FIG. 2 is a schematic view depicting an example of a system according to the system aspect of present invention.

Referring to FIG. 2, the device 1 may further comprise a display member 18 configured to display the pressure measured by the pressure sensing member, i.e. the tissue response pressure. The display member can be an LCD panel, which can be separate from or part of the control unit 13. The display member 18 facilitates monitoring of the tissue response pressure by an operator. Such display member 18 may either show a current value of the tissue response pressure only, or may alternatively or also show how the tissue response pressure develops over time. In other words the display member 18 is in one embodiment configured to display the pressure measured by the pressure sensing member as a function of time. The display member may be digital or analog. In case the display member only shows a current value of the tissue response pressure the operator has to monitor the time development of the signal in order to be able to draw any conclusions regarding the nasal pathology. If the development of the tissue response pressure over time is shown, e.g. on a computer screen or on an XY-plotter, the evaluation of nasal pathology for the operator is facilitated. In both cases however, it is the operator who, based on experience and/or training, draws conclusions regarding the health of the patient.

With reference to FIG. 2, a specific example of a system according to the system aspect of the present invention will now be discussed. The system comprises a device 1 having an inflatable member 2 optionally provided with pressure sensors 5 at the surface. The inflatable member 2 is arranged around an expansion member 3 as described above. Fluid such as air enters the system via an inlet 6. In a pressure regulator 7, the fluid is pressurized before being supplied to the device 1 via tubing 8. One example of a pressure regulator 7 is a pressure pump. Before supply to the device 1, the fluid may optionally pass a frequency and amplitude regulator 9. One example of a frequency and amplitude regulator 9 is an oscillation pump. If present, the frequency and amplitude regulator 9 provides vibrations having a desired frequency and amplitude to the pressurized fluid, which subsequently via tubing 10 and expansion member 3 is supplied to the device 1. Tubing 10 is provided with a safety valve 11 for releasing fluid should the pressure within the inflatable member 2 exceed a certain maximum value. For controlling the system pressure, and in some instances measure the inner pressure of the inflatable member 2 representing the tissue response pressure, an external pressure sensor 12 may be provided.

The control unit 13 comprises a data collection module (not shown) for obtaining an input signal reflecting a measure of the tissue response pressure exerted on the inflatable member 2 of the device 1 according to the invention. The control unit 13 may in some embodiments receive the input signal via line 17 from the pressure sensors 5 arranged on the device 1. The pressure exerted by the nasal tissue onto the inflatable member 2 may be monitored continuously or according to a predetermined schedule. The measured pressure may furthermore be stored in the data collection module.

In addition, the system may comprise a display member 18 that is configured to display the pressure measured by the pressure sensors 5. The display member 18 may be integrated with control unit 13, as shown in FIG. 2, or may be arranged as a separate unit. The display member 18 may be configured to display the pressure measured by the pressure sensing member as a current value, as a distinct value at a certain time point, or as a function of time.

The measured pressure is further analyzed by a pressure analyzing module (not shown), optionally arranged within the control unit 13. The pressure analyzing module identifies plateaus and decreases in the measured pressure signal, collected for example during a period of from 1 to 10 minutes.

A rhinitis detection module (not shown) is further provided for comparison of identified plateaus and decreases in the measured pressure to e.g. a predetermined boundary condition or to a reference pressure curve. Rhinitis is hence detected.

The control unit 13 of the system is further connected to the pressure regulator 7 via line 14. Information regarding the applied pressure is thus forwarded from the pressure regulator 7 to the control unit 13 via said line 14. The application of pressure may in addition be centrally controlled from control unit 13.

If present, the frequency and amplitude regulator 9 communicates with the control unit 13 via line 15. Information is forwarded from the optional frequency and amplitude regulator 9 to the control unit via the line 15, and commands are transmitted from the control unit 13 to the frequency and amplitude regulator 9 via said line 15.

It should be understood that the data collection module, the pressure analyzing module and the rhinitis detection module may be integrated within a common control unit 13 as described above, or can be arranged separately from each other in, e.g. separate control units.

One example of a control unit 13 is a microprocessor comprising suitable peripheral I/O capability executing software, e.g. for analyzing the input signal and for determining how to adjust the pressure and optionally the frequency and the amplitude. It is contemplated that other types of a control unit 13 may be used, such as e.g. a personal computer.

Figure 3:
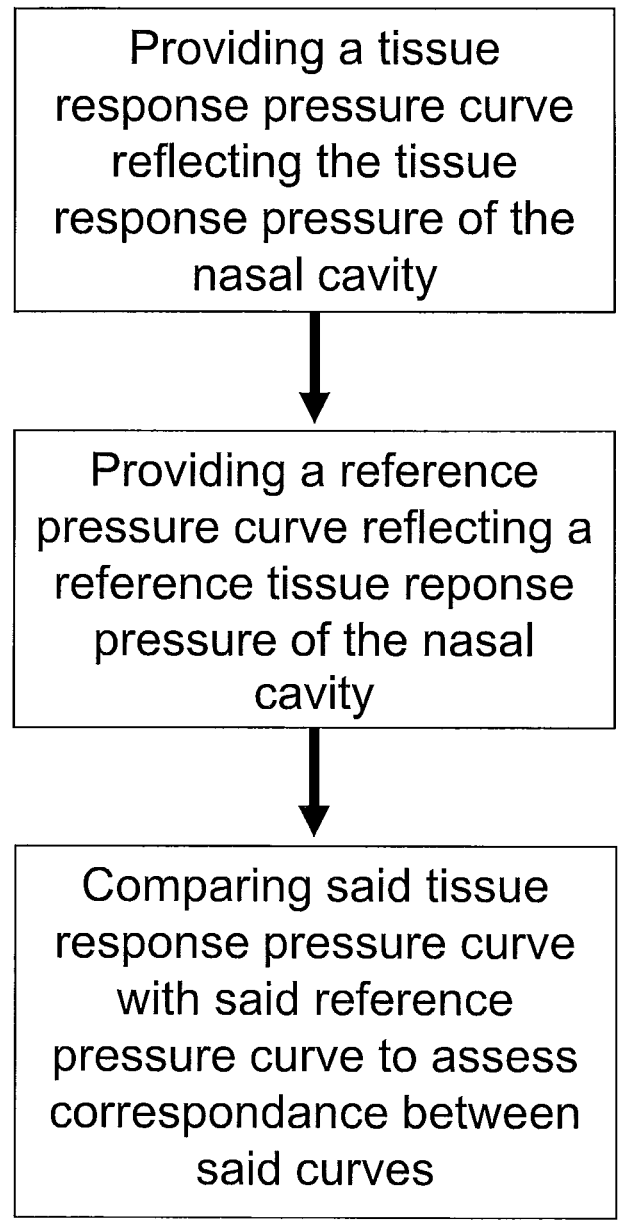
FIG. 3 is a flow chart indicating the steps comprised in one embodiment of a tissue response pressure analyzing method according to the present invention.

With reference to FIG. 3, a specific example of a method according to a method aspect of the present invention will now be discussed. A tissue response pressure curve is firstly provided. The tissue response pressure curve reflects the tissue response pressure of the nasal cavity of a human subject over a period of time. The tissue response pressure has thus been measured and collected separately from the current exemplary method. In other exemplary methods, an input signal reflecting a tissue response pressure is obtained and a tissue response pressure curve is created by adapting a curve to individual values of the input signal obtained over a period of time, or by sampling said input signal over a period of time. By adapting a curve to the individual values, the comparison to a reference curve may be easier to perform, especially if the reference curve is formulated in the same way. This can furthermore be an efficient way to remove noise from the signal. Use of sampled values eliminates the need for a parameterized representation.

A reference pressure curve is thereafter provided. This reference pressure curve reflects a reference tissue response pressure of the nasal cavity over a reference period of time. This reference pressure curve can be obtained according to procedures described herein.

Subsequently, the curves are compared. The tissue response pressure curve is compared to said reference pressure curve in order to assess correspondence between the two. The comparison may be of relevance for a subsequent detection step wherein rhinitis is detected by, e.g. determining whether there is correspondence or whether the tissue response pressure curve lies within a predetermined tolerance interval; determining whether at least parts of the tissue response pressure curve exceeds said tolerance interval, and determining whether at least parts of the tissue response pressure curve falls below said tolerance interval.

Rhinitis Detection in Human Subjects

By applying a static pressure in a balloon inserted into the nasal cavity and monitoring the resulting pressure over time, rhinitis can be detected. Observations from tissue response pressure measurements in the nasal cavities of human patients are accounted for in the following.

The patients subjected to the measurements have been categorized into three general groups, B), C) and D). The first group A) represents healthy patients (i.e. not suffering from rhinitis).

The second group B) represents patients suffering from a subtype of rhinitis. This group of patients is commonly referred to as blockers. Blockers experience a stuffy nose, sometimes in combination with sneezes. These patients have typically been treated with pharmaceuticals (e.g. cortisone) with a success rate below 50% in the non-allergic cases. An alternative treatment option is invasive tissue destructive surgery. This group constitutes about 80% of the rhinitis patients.

The third group C) also represents patients suffering from a subtype of rhinitis, and this group is commonly referred to as sneezers. Sneezers, as the name implies, sneeze a lot. Sneezing is often accompanied by increased secretion in the nose. This group constitutes about 10% of the rhinitis patients.

The fourth group D) also represents patients suffering from a subtype of rhinitis. This group is commonly denoted runners. Typical symptoms include a lot of secretion in the nose. The runners represent the remaining 10% of the rhinitis patients and are the most problematic to treat. There are most likely several pathologies contributing to this type of syndrome, for instance connected to aging. These patients are often therapy resistant.

Figure 4:
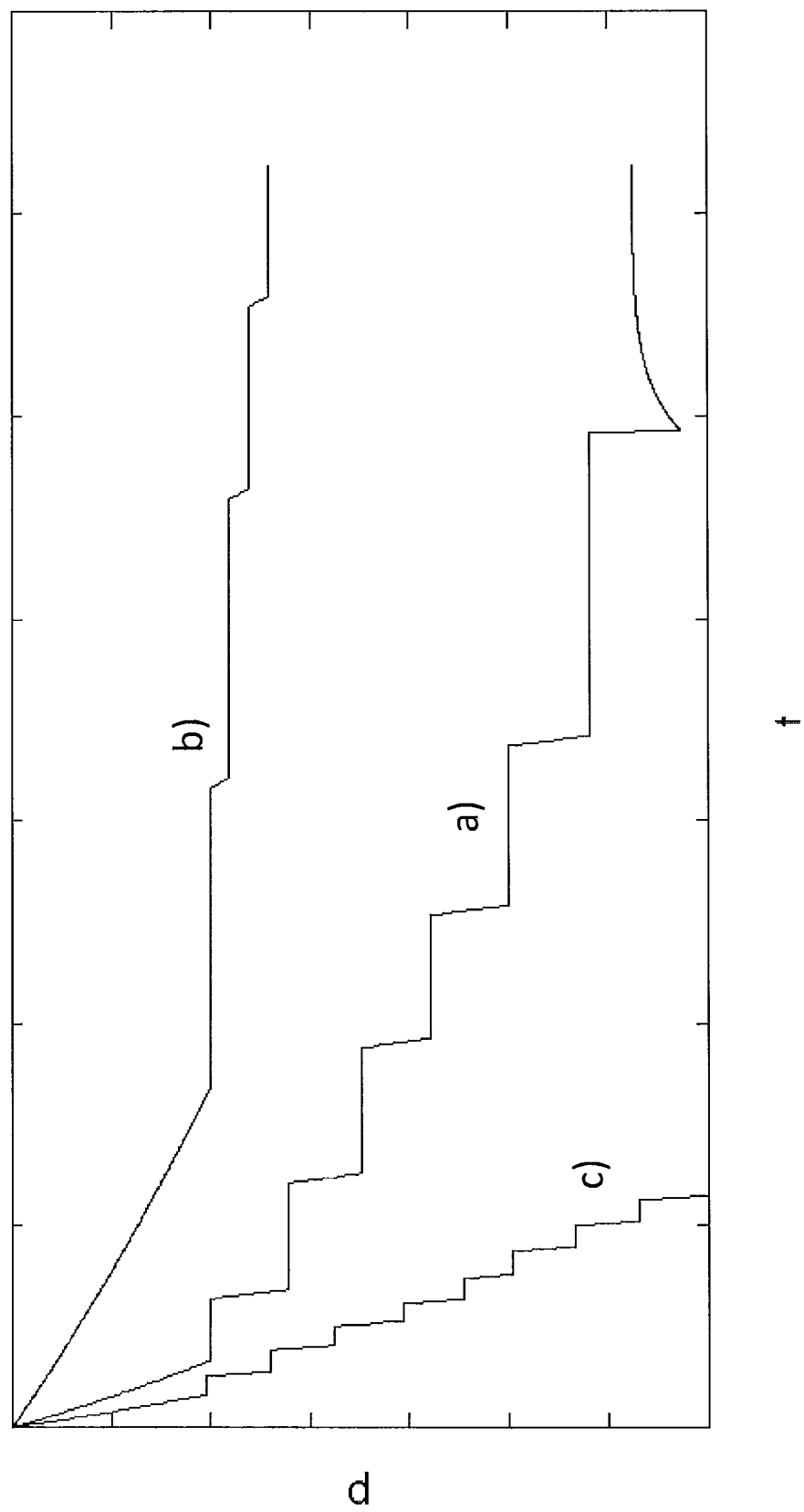
FIG. 4 is a pressure curve showing exemplary measured tissue response pressure curves a)-c) representative of different health conditions.

In FIG. 4 representative tissue response pressure curves are shown, wherein a) represents the healthy group A), b) represents the blockers B) and c) represents the sneezers c).

The inflatable member used was a balloon which in an expanded state had a diameter of approximately 1.5 cm and a length of 5 cm. The balloon was connected with a tubing having a length of approximately 15 cm. The tubing and the balloon were connected to each other such that one end of the tubing resided within the balloon, having a length of maximally 4 cm to simplify introduction into the nasal cavity. The tubing supplied air to the balloon for expanding the same. The other end of the tubing was connected via a three-way cock to a graduated syringe (20 ml) as well as to another tubing, which was connected to a closed air system.

The closed air system was connected to a flexible membrane, which during some pressure measurements was oscillated with a variable frequency in the interval 10-100 Hz by means of a motor. The air pressure could be varied in a controlled manner within a pressure interval of 5-180 mbar. The amplitude of the oscillating membrane could be varied in a controlled manner (in arbitrary but reproducible units). Prior to use, the balloon was provided with a hygienic protective cover, consisting of a finger from a disposable glove. The hygienic protective cover was dipped in a paraffin solution prior to each introduction into a nasal cavity.

It was discovered that in a human patient representing group A), the pressure initially dropped to a level of about 100 mbar. Thereafter sudden pressure decreases of approximately 10 mbar were observed. The pressure decreases occurred repeatedly with periods of nearly constant pressure in between. The decreases were observed at increasing time intervals of about 10 seconds. After a period of approximately 1 minute, a first saturation pressure was reached wherein the measured pressure was in the range of from 25 to 30 mbar. The applied pressure was then lowered to approximately 5 mbar. Following a smooth recovery, the measured tissue pressure was stabilized at a second saturation pressure of approximately 15 mbar.

The interpretation of pressure measurements on healthy persons of group A) is that the sudden pressure decreases correspond to sphincters opening up which leads to less blood filling in the nasal mucosa. The smooth recovery seen after the deliberate pressure decrease is in turn believed to correspond to refilling of the vessels and resumed function of the sphincters.

In the second group B), the initial pressure decrease was slower compared to the healthy reference, see FIG. 4 b). This was followed by relatively small decreases in pressure and sometimes relatively long periods of nearly constant pressure. These periods of nearly constant pressure are referred to as plateaus. The relatively small decreases and long plateaus are hypothesized to be due to sphincters being stuck and unable to open in the way they do in healthy subjects.

In the third group C), tissue response pressure dropped comparatively fast with relatively short plateau periods between the pressure drops. The reason for this might be that the sphincters could only withstand the applied pressure for a short period of time.

In the fourth group D), tissue response pressure curves similar to those of group A) were observed. To distinguish this group of patients from the other groups, vibrations were administered via the inflatable member to the nasal cavity in patients representing all the defined groups. The vibrations immediately provoked reactions in the rhinitis patients but not in the healthy humans. The reactions displayed by the rhinitis patients were, among others, frequent sneezing, increased secretion in nose and/or eyes, itches and a sensation of stuffed nose in the cavity not being subjected to vibrations. The healthy humans, on the other hand, merely noted that vibrations were applied without showing any signs of over sensibility. The initially strong reaction in the rhinitis patients to the applied vibrations subsequently diminished.

After being subjected to vibration administration, essentially as described in WO 2008/138997, the rhinitis patients displayed the same type of tissue response pressure curves as those of group A). It is believed that when the initially strong reaction of the rhinitis patients diminished, the patients were relieved of his/her symptoms.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for detecting rhinitis, comprising the steps of:
introducing an inflatable member into a nasal cavity of a human subject;
expanding the inflatable member within the nasal cavity such that the inflatable member abuts against a tissue of the nasal cavity;
measuring a pressure exerted on the inflatable member by the tissue of the nasal cavity over a period of time to create a measured pressure curve;
analyzing the measured pressure curve to detect rhinitis, wherein the step of analyzing comprises the steps of:
identifying plateaus and decreases in said measured pressure curve; and
comparing said plateaus and decreases to at least one predetermined boundary condition;
characterizing the plateaus and decreases by at least one curve property selected from amplitude, rate of change or frequency; and
detecting a subtype of rhinitis, the step of detecting the subtype of rhinitis comprising at least one of the following sub-steps:
determining whether any individual values of any one of the curve properties surpasses a predetermined maximum threshold for that particular curve property, and
determining whether any individual values of any one of the curve properties goes below a predetermined minimum threshold for that particular curve property.

2. The method according to claim 1, wherein the analyzing comprises providing a reference pressure curve and comparing the measured pressure curve to the reference pressure curve.

3. The method according to claim 2, further comprising one of determining whether the measured pressure curve corresponds to the reference pressure curve or lies within a predetermined tolerance interval; determining whether at least part of the measured pressure curve exceeds the tolerance interval, or determining whether at least part of the measured pressure curve falls below the tolerance interval.

4. The method according to claim 2, wherein the reference pressure curve is selected from a previously obtained measured pressure curve; an average of at least two previously obtained measured pressure curves; a fit of a model to at least one measured pressure curve; or a theoretically calculated reference pressure curve.

5. The method according to claim 1, further comprising imparting vibrations to the tissue in the nasal cavity via the inflatable member.

6. The method according to claim 5 further comprising determining compliance of the tissue to the imparted vibrations.

7. The method according to claim 5, further comprising detecting peaks corresponding to sneezes in the pressure exerted on the inflatable member.

8. The method according to claim 7, further comprising determining whether a peak frequency surpasses a predetermined peak threshold.

9. The method according to claim 1, wherein the inflatable member abuts against the tissue of the nasal cavity at a pressure of between 100 and 180 mbar.

10. The method according to claim 1, wherein the period of time is between 1 and 10 minutes.

11. The method according to claim 1, wherein the measured pressure curve is created by a method comprising either storing time and pressure value pairs or fitting a model to time and pressure value pairs.

12. The method according to claim 1, wherein the inflatable member is present in a device, comprising: an inflatable member that, in a first state, is configured to be introducible into the nasal cavity of the human subject; an expansion member configured to expand the inflatable member to an expanded, second state within the nasal cavity such that the inflatable member abuts against the tissue of the nasal cavity.

13. The method according to claim 12, wherein the device further comprises a pressure sensor configured to measure a pressure exerted on the inflatable member by the tissue of the nasal cavity.

14. The method according to claim 12, wherein the expansion member further comprises a tubular structure comprising an end portion arranged freely within said inflatable member said end portion comprising at least one opening for fluid communication with the inflatable member.

* * * * *